Figure 1:
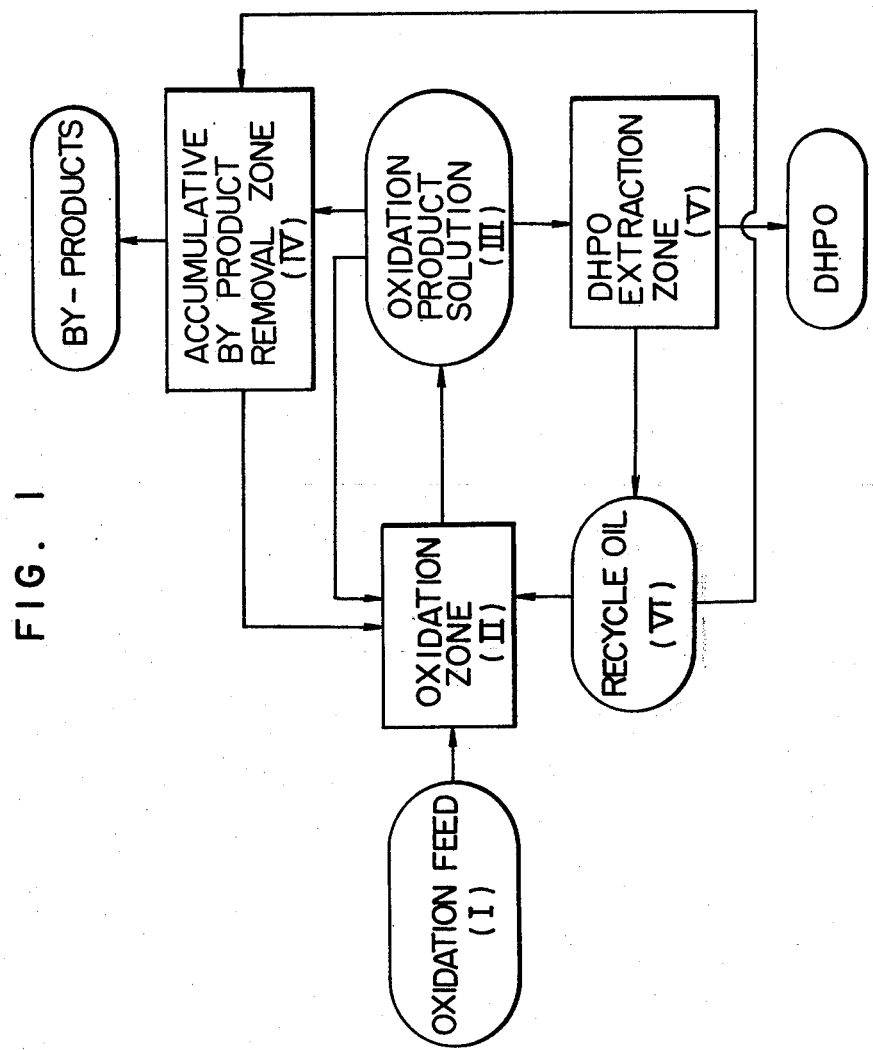

United States Patent
Suda et al.

[11] 3,950,431
[45] Apr. 13, 1976

[54] PROCESS FOR REMOVING IMPURITIES IN AN OXIDATION MIXTURE

[75] Inventors: Hideaki Suda, Takaishi; Iwao Dohgane, Nishinomiya; Takashi Chinuki, Toyonaka; Kenji Tanimoto; Hirokazu Hosaka, both of Minoo; Yukimichi Nakao, Kobe; Yuji Ueda, Izumiotsu; Seiya Imada, Sakai; Hideki Yanagihara, Toyonaka; Kunihiko Tanaka, Ibaragi, all of Japan

[73] Assignee: Sumitomo Chemical Company, Limited, Osaka, Japan

[22] Filed: Sept. 20, 1973

[21] Appl. No.: 399,248

[30] Foreign Application Priority Data
Nov. 21, 1972 Japan.............................. 47-117448

[52] U.S. Cl...... 260/610 A; 260/590 R; 260/618 R; 260/669 R
[51] Int. Cl.².................................... C07C 179/02
[58] Field of Search............ 260/610 A, 590, 610 B, 260/618 R; 210/423

[56] References Cited
UNITED STATES PATENTS

| | | | |
|---|---|---|---|
| 2,812,357 | 11/1957 | Webster et al.................. | 260/610 A |
| 2,856,432 | 10/1958 | Conner.......................... | 260/610 A |

FOREIGN PATENTS OR APPLICATIONS

| | | | |
|---|---|---|---|
| 649,827 | 10/1962 | Canada.......................... | 260/610 A |
| 786,340 | 11/1957 | United Kingdom............. | 260/610 A |

*Primary Examiner*—James O. Thomas, Jr.
*Assistant Examiner*—W. B. Lone
*Attorney, Agent, or Firm*—Stevens, Davis, Miller & Mosher

[57] ABSTRACT

Impurities, that is, by-products, in an oxidation product solution obtained by oxidation of diisopropylbenzene by molecular oxygen or in the oxidation product solution freed from diisopropylbenzene dihydroperoxide, are removed by extracting the by-products such as carbinols, ketones and styrenes from the solution with a mixture of an aqueous alkaline solution and at least one of alcohols having 1 to 3 carbon atoms such as methanol, ethanol, and isopropanol, as an extracting reagent at a temperature of 20° to 80°C.

12 Claims, 1 Drawing Figure

PROCESS FOR REMOVING IMPURITIES IN AN OXIDATION MIXTURE

This invention relates to a process for treating an oxidation product solution resulting from oxidation of diisopropylbenzene by molecular oxygen, and more particularly to a process for removing impurities from an oxidation product solution resulting from oxidation of diisopropylbenzene by molecular oxygen or the oxidation product solution freed from diisopropylbenzene dihydroperoxide, which will be hereinafter referred to as DHPO, which comprises extracting by-products resulting from the oxidation of diisopropylbenzene from the solution with a mixture of an aqueous alkaline solution and at least one of alcohols having 1 to 3 carbon atoms.

It is well known that an oxidation product solution resulting from oxidation of diisopropylbenzene is subjected to extraction with an aqueous alkaline solution, thereby separating DHPO from the solution, and then DHPO is cleaved using an acid catalyst to obtain resorcinol and/or hydroquinone. The oxidation reaction is regarded as consecutive reactions, wherein diisopropylbenzene monohydroperoxide, which will be hereinafter referred to as MHPO, is formed at first from diisopropylbenzene, and then further oxidized to DHPO. That is, only the desired DHPO cannot be selectively obtained, and MHPO which is deemed as an intermediate, is always formed together with DHPO. Even if MHPO is presumed to be a raw material, yield of DHPO from diisopropylbenzene or MHPO is 30 to 90% according to the prior art, and it is hard to obtain DHPO quantitatively. In other words, DHPO cannot be obtained without any formation of by-products.

It is also well known that after the oxidation product solution is subjected to extraction with the aqueous alkaline solution to separate DHPO from the solution, the raffinate solution containing unreacted diisopropylbenzene, MHPO and a large amount of other oxidation by-products is recycled to the oxidation reaction. Through experiences in carrying out the operations of oxidation, extraction and recycling, the present inventors have found that recycled diisopropylbenzene and MHPO can contribute again to the oxidation reaction as a raw material and an intermediate, respectively, but other oxidation by-products returned to the oxidation reaction system at the same time are accumulated in the reaction system, giving no contribution to the oxidation reaction but considerably impairing an efficiency of the oxidation reaction itself. That is, it is necessary to positively remove compounds having an accumulative tendency, that is, the compounds that cannot be removed in the oxidation step or successive extraction step, from the oxidation product solution. If the operations of oxidation, extraction and recycling are continued without any removal of these compounds having an accumulative tendency, discontinuation of the oxidation reaction or failure of extraction will be brought about due to the contamination by the accumulated by-products. Even if there appears none of such worst cases but the accumulated by-products can be kept at an equilibrium concentration, oxidation reaction or extraction will be much adversely influenced thereby.

If a series of operations to obtain peroxides by oxidation of diisopropylbenzene and obtain the desired DHPO from the resulting oxidation product solution by extraction is carried out continuously as well as economically, it is essential to prevent accumulation of these by-products in the reaction system, and continuous and economical oxidation cannot be attained in the production of DHPO without any prevention of such by-product accumulation.

The present inventors have studied these problems and clarified the by-products, especially accumulative by-products in the oxidation reaction, which have not been apparent so far. Further, the present inventors have studied processes for preventing the accumulation of these by-products, that is, removing these by-products.

As a result, the present inventors have found that the accumulative by-product compounds resulting from the oxidation of diisopropylbenzene include carbinols such as isopropylphenyldimethylcarbinol, di(2-hydroxy-2-propyl)benzene, and acetylphenyldimethylcarbinol, ketones such as acetylisopropylbenzene, diacetylbenzene, and acetylisopropenylbenzene, and styrenes such as isopropylisopropenylbenzenes, and diisopropenylbenzene, and further that an extraction by means of an alcohols-alkali-water system is effective for removing these carbinols, ketones and sytrenes from the oxidation product solution.

According to the present invention, the oxidation by-products such as carbinols, ketones and styrenes contained in the oxidation product solution are extracted into an aqueous layer by subjecting an oxidation product solution of diisopropylbenzene or the solution freed from DHPO with a mixture of an aqueous alkaline solution and at least one of alcohols having 1 to 3 carbon atoms and thus the by-products are removed from the oxidation product solution by separation of the aqueous layer and the oxidation oil layer.

After the by-products have been removed from the oxidation product solution or the solution freed from DHPO in this manner, the resulting solution can be recycled to the oxidation zone without any accumulation of these by-products within the reaction zone. Therefore, the interruption of the oxidation reaction itself or the failure of the successive extraction and separation due to the contamination by the accumulated by-products is never brought about, so that the oxidation reaction proceeds very smoothly, and the successive operation can be carried out very easily.

That is to say, it can be said that the recyclic use of raw materials has been made possible in a series of the oxidation reaction and the successive extraction and separation for the first time according to the present invention. In this respect, the present invention has a very great industrial significance.

In the present invention, a three-component solvent of alcohol-alkali-water is used as an extracting reagent. Only one kind of alcohol or a mixture of two or more kinds of alcohols can be used in the present invention.

It is desireble that the extracting reagent has a higher alcohol content to remove the by-products, but in that case separation of the aqueous layer and the oxidation oil layer will be difficult with higher alcohol content. On the other hand, the aqueous layer can be more easily separated from the oxidation oil layer with higher water content, but the extraction efficiency of the by-products is decreased. Alcohol and water used in the extracting reagent act contradictorily, but higher alcohol content is preferable to remove the by-products, and a small amount of alkali is necessary for improving the separability of the aqueous layer and the oxidation oil layer.

As the extracting reagent, an aqueous solution containing 10 to 80% by weight of alcohol and 0.05 to 1.0% by weight of alkali is usually used for this purpose. The extraction temperature is 20° to 80°C, but the extraction is usually in the most cases carried out at the normal temperature.

Ratio of the components of the extracting reagent is properly selected from the aforesaid range, in view of the composition of the oxidation product solution, separability of the extracting reagent, extraction temperature, etc.

Alcohols used in the present invention include, for example, methanol, ethanol, isopropanol, etc., and alkali compounds used in the present invention include caustic soda, sodium carbonate, etc. A weight ratio of the extracting reagent to the oxidation product solution is 0.3 to 3.0, preferably 0.8 to 2.0.

When a mixture of two or more kinds of alcohols is used, the mixing ratio of the alcohols can be selected freely.

As described above, an object of the present invention is to provide a process for removing accumulative oxidation by-products more efficiently and economically even in an industrial scale in the production of DHPO by oxidation of diisopropylbenzene. The oxidation reaction can be carried out very favorably by applying the present invention to the process for producing DHPO from diisopropylbenzene.

One embodiment of incorporating the present process into the oxidation process is explained by way of the accompanying drawing.

FIGURE is a block diagram showing a series of oxidation, removal of accumulative by-products, extraction of DHPO and recycle of the product solution to the oxidation system.

In the FIGURE, an oxidation feed solution (I) is supplied to an oxidation zone (II), where oxidation reaction is carried out and an oxidation product solution (III) is obtained. The oxidation product solution may be partly recycled to the oxidation zone (II), and partly led to an accumulative by-product removal zone (IV). A portion of entire amount of the oxidation product solution (III) is led to DHPO extraction zone (V), where the solution is separated into a portion consisting mainly of DHPO and a recycle oil (VI) consisting mainly of MHPO. The resulting recycle oil (VI) may be partly returned to the oxidation zone (II) or partly led to the accumulative by-product removal zone (IV), or the entire amount of the recycle oil (VI) may be led to the oxidation zone (II) provided that a portion of the oxidation product solution (III) is led to an accumulative by-product removal system (IV), or the accumulative by-product removal zone (IV). The oxidation product solution (III) and the recycle oil (VI) led to the accumulative by-product removal zone (IV) are subjected to removal of the accumulative by-products therein, and then returned to the oxidation zone (II). Thus, the oxidation reaction can be carried out without any adverse influence by the accumulative by-products even if MHPO is recycled.

The present invention can be utilized also in the production of DHPO in a process for producing resorcinol and hydroquinone from diisopropylbenzene.

Thus, the present invention also provides a process for continuously producing dihydroperoxides of diisopropylbenzene by feeding diisopropylbenzene to an oxidation zone, where the diisopropylbenzene is oxidized with molecular oxygen to produce dihydroperoxides thereof, leading a portion or entire amount of the oxidation product solution to a dihydroperoxide extraction zone, where the solution is separated into an aqueous layer consisting mainly of dihydroperoxides of diisopropylbenzene and an oily layer containing monohydroperoxide of diisopropylbenzene, the residual part of the oxidation product solution being recycled to the oxidation zone, and recycling a portion or entire amount of the oily layer to the oxidation zone, characterized in that a portion of the residual part of the oxidation product solution, and a portion or entire amount of the oily layer are led to an accumulative by-product removal zone, where by-products formed by the oxidation are extracted with a mixture of an aqueous alkaline solution and at least one of alcohols having 1 to 3 carbon atoms as an extracting reagent to obtain an aqueous layer containing the by-products and an oily layer substantially freed from the by-products, and the oily layer is recycled to the oxidation zone.

Now, the present invention will be described in detail by way of Examples but not limited thereto, wherein parts are all by weight.

EXAMPLE 1

100 Parts of methyl alcohol and 100 parts of water containing 0.2 parts of caustic soda are added to 100 parts of an oxidation product solution containing 17 parts of carbinols, 9 parts of ketones and 2 parts of styrenes, the balance being hydroperoxides, which has been obtained by ordinary oxidation of diisopropylbenzene with air, and the mixture is stirred in a glass reactor at room temperature for 30 minutes. Then, the mixture is left standing and separated into 87 parts of an oil layer and 209 parts of an aqueous layer. By-products in the oil layer are reduced to 2 parts of carbinols, 0.7 parts of ketones and 0.4 parts of styrenes.

EXAMPLE 2

80 Parts of ethyl alcohol, 20 parts of water and 0.2 parts of caustic soda are added to 100 parts of diisopropylbenzene containing 12 parts of carbinols, 4 parts of ketones, and 0.7 parts of styrenes, the balance being hydroperoxides of diisopropylbenzene, and the resulting mixture is stirred at 40°C for 10 minutes. Then, the mixture is separated, whereby 107.2 parts of an oil layer is obtained. By-products in the resulting oil layer are 2.4 parts of carbinols, 0.9 parts of ketones and 0.4 parts of styrenes.

EXAMPLE 3

20 Parts of methyl alcohol, 20 parts of n-propyl alcohol, 60 parts of water and 0.3 parts of caustic soda are added to 100 parts of diisopropylbenzene containing 15 parts of carbinols, 2 parts of ketones and 0.9 parts of styrenes, the balance being hydroperoxides of diisopropylbenzene, and the resulting mixture is stirred at 65°C for 20 minutes, and then separated, whereby 103.7 parts of an oil layer is obtained. By-products in the oil layer are 3.7 parts of carbinols, 0.6 parts of ketones and 0.6 parts of styrene.

REFERENCE EXAMPLE

An oxidation product solution having the same composition as used in Example 1 was separated into an aqueous layer containing DHPO and an oil layer containing MHPO, unreacted diisopropylbenzene and other impurities with a NaOH-water system according to the well known method. Diisopropylbenzene was freshly added to the oil layer, and the resulting mixture was used as an oxidation feed solution, and oxidation reaction was carried out again according to the ordinary oxidation process. After the reaction, the resulting oxidation product solution was analyzed to determine an oxidation yield of the reaction. The oxidation yield was found to be 51.7%.

The oxidation yield herein referred to is a percent ratio of moles of DHPO formed in the oxidation to sum total of moles of diisopropylbenzene and MHPO consumed in the oxidation.

The aforesaid oxidation reaction was continued for 10 hours under constant conditions, and after the completion of the reaction, 19 parts of DHPO was formed.

The resulting oxidation product solution was subjected again to NaOH extraction to remove DHPO and obtain a recycle oil for reuse in the oxidation reaction, but paste-like deposits consisting mainly of carbinols were formed and a clogging took place at the vessel, resulting in failure of NaOH extraction.

An oil layer freed from the impurities, which was obtained in Example 1 was subjected to the NaOH extraction in the same manner as above, to separate DHPO therefrom, and the resulting raffinate oil layer was freshly admixed with diisopropylbenzene to adjust the ratio of MHPO to diisopropylbenzene contained in the oxidation feed solution equal to that of aforesaid oxidation feed solution. Oxidation reaction was carried out in the same reactor under the same conditions as above.

After the oxidation, the oxidation yield was determined by analysis of the resulting oxidation product solution, and found to be 78.5%. In that case, 27 parts of DHPO was obtained in the oxidation reaction.

The resulting oxidation product solution was subjected again to the NaOH extraction to remove DHPO, and the raffinate oil layer was reused as a portion of the oxidation feed solution. A series of these operations of oxidation reaction, by-product removal and DHPO extraction was repeated 38 times, but the oxidation reaction was carried out stably in constant oxidation yield through these repetitions, and no paste-like deposits were formed in the NaOH extraction. Thus, these operations could be carried out without any trouble.

What is claimed is:

1. A process for removing carbinols, ketones and styrenes impurities from an oxidation product obtained by oxidation of diisopropylbenzene by molecular oxygen which comprises extracting at a temperature of 20° to 80°C by-products formed by the oxidation from the solution with an aqueous extracting reagent solution consisting essentially of 10 to 80% by weight of at least one alcohol having one to three carbon atoms and 0.05 to 1.0% by weight of sodium hydroxide or sodium carbonate, separating into an aqueous layer containing the by-products and an oily layer substantially freed from the by-products and containing both diisopropylbenzene monohydroperoxide and diisopropylbenzene dihydroperoxide as the hydroperoxides.

2. A process according to claim 1, wherein the carbinols are isopropylphenyldimethylcarbinol, di-(2-hydroxy-2-propyl)benzene, and acetylphenyldimethylcarbinol; the ketones are acetylisopropylbenzene, diacetylbenzene, and acetylisopropenylbenzene; and the styrenes are isopropylisopropenylbenzene and diisopropenylbenzene.

3. A process according to claim 1, wherein the alcohol is methanol, ethanol or isopropanol.

4. A process according to claim 1, wherein 0.3 to 3.0 times by weight of the extracting reagent is added to the solution, based on the weight of the solution.

5. A process according to claim 4, wherein 0.8 to 2.0 times by weight of the extracting reagent is added to the solution, based on the weight of the solution.

6. A process for removing carbinols, ketones and styrenes impurities from an oxidation product solution obtained by oxidation of diisopropylbenzene by molecular oxidation which has been freed from diisopropylbenzene dihydroperoxide which comprises extracting at a temperature of 20° to 80°C by-products formed by the oxidation from the solution with an aqueous extracting reagent solution consisting essentially of 10 to 80% by weight of at least one alcohol having one to three carbon atoms and 0.05 to 1.0% by weight of sodium hydroxide or sodium carbonate, separating into an aqueous layer containing the by-products and an oily layer substantially freed from the by-products and containing diisopropylbenzene monohydroperoxide.

7. A process according to claim 6, wherein the by-products are carbinols, ketones and styrenes.

8. A process according to claim 6, wherein the alcohol is methanol, ethanol or isopropanol.

9. A process according to claim 6, wherein 0.3 to 3.0 times by weight of the extracting reagent is added to the solution, based on the weight of the solution.

10. A process according to claim 9, wherein 0.8 to 2.0 times by weight of the extracting reagent is added to the solution, based on the weight of the solution.

11. In a process for continuously producing dihydroperoxides of diisopropylbenzene by feeding diisopropylbenzene to an oxidation zone, where the diisopropylbenzene is oxidized with molecular oxygen to produce dihydroperoxides thereof, leading the oxidation product solution to a dihydroperoxide extraction zone, where the solution is separated into an aqueous layer consisting mainly of dihydroperoxides of diisopropylbenzene and an oily layer containing monohydroperoxide of diisopropylbenzene, and recycling the oily layer to the oxidation zone, the improvement which comprises leading at least a portion of the oily layer prior to recycling to the oxidation zone to an accumulative carbinols, ketones and styrenes by-product removal zone where by-products formed by the oxidation are extracted at a temperature of 20° to 80°C with an aqueous extracting reagent solution consisting essentially of 10 to 80% by weight of at least one alcohol having 1 to 3 carbon atoms and 0.05 to 1.0% by weight of sodium hydroxide or sodium carbonate to obtain an aqueous layer containing the by-products and an oily layer substantially freed from the by-products, and the oily layer is recycled to the oxidation system.

12. In a process for continuously producing dihydroperoxides of diisopropylbenzene by feeding diisopropylbenzene to an oxidation zone, where the diisopropylbenzene is oxidized with molecular oxygen to produce dihydroperoxides thereof, leading a portion of the oxidation product solution to a dihydroperoxide extraction zone, where the solution is separated into an aqueous layer consisting mainly of dihydroperoxides of diisopropylbenzene and an oily layer containing monohydroperoxides of diisopropylbenzene, the residual part of the oxidation product solution being recycled to the oxidation zone, and recycling the oily layer to the oxidation zone, the improvement which comprises leading a portion of the residual part of the oxidation product solution, and at least a portion of the oily layer prior to recycling to the oxidation zone to an accumulative carbinols, ketones and styrenes by-product removal zone where by-products formed by the oxidation are extracted at a temperature of 20° to 80°C with an aqueous extracting reagent solution consisting essentially of 10 to 80% by weight of at least one alcohol having 1 to 3 carbon atoms and 0.05 to 1.0% by weight of sodium hydroxide or sodium carbonate to obtain an aqueous layer containing the by-products and an oily layer substantially freed from the by-products, and the oily layer is recycled to the oxidation system.

* * * * *